United States Patent
Sojomihardjo et al.

(10) Patent No.: US 6,565,842 B1
(45) Date of Patent: *May 20, 2003

(54) CROSSLINKABLE POLYPEPTIDE COMPOSITIONS

(75) Inventors: Soebianto A. Sojomihardjo, West Covina, CA (US); Neil P. Desai, Los Angeles, CA (US); Paul A. Sandford, Los Angeles, CA (US); Patrick Soon-Shiong, Los Angeles, CA (US); Shubhi Nagrani, Torrance, CA (US)

(73) Assignee: American Bioscience, Inc., Santa Monica, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/484,724

(22) Filed: Jun. 7, 1995

(65) Prior Publication Data (65)

(51) Int. Cl.$^7$ ................ A61K 47/42; C07K 1/113; C07K 17/04; C07K 17/08

(52) U.S. Cl. .............. 424/85.1; 424/85.2; 424/85.4; 424/94.3; 424/178.1; 424/425; 424/486; 424/487; 435/180; 435/182; 514/2; 514/3; 514/6; 514/8; 514/12; 514/21; 525/54.1; 530/345; 530/410; 530/815; 530/817

(58) Field of Search .................. 525/54.7, 54.11; 514/3, 2, 6, 8, 12, 21, 44; 526/238.1; 435/177, 180, 182; 424/1.25, 1.29, 85.1, 85.2, 85.4, 93.1, 93.7, 94.1, 94.3, 130.1, 178.1, 184.1, 425, 477, 478, 486, 487, 491, 492, 499

(56) References Cited

U.S. PATENT DOCUMENTS

| | | | | |
|---|---|---|---|---|
| 3,969,287 A | * | 7/1976 | Jaworek et al. | 260/8 |
| 4,511,478 A | * | 4/1985 | Nowinski et al. | 525/54.1 |
| 4,511,748 A | | 4/1985 | Nowinski et al. | 210/691 |
| 4,576,817 A | * | 3/1986 | Montgomery et al. | 424/94 |
| 4,798,786 A | * | 1/1989 | Tice et al. | 435/177 |
| 5,204,108 A | * | 4/1993 | Illum | 424/434 |
| 5,362,478 A | | 11/1994 | Desai et al. | 424/9 |
| 5,439,686 A | | 8/1995 | Desai et al. | 424/451 |
| 5,529,914 A | * | 6/1996 | Hubbell et al. | 435/182 |
| 5,554,366 A | * | 9/1996 | Rawlings et al. | 424/78.03 |
| 5,573,934 A | * | 11/1996 | Hubbell et al. | 435/177 |
| 5,837,747 A | * | 11/1998 | Soon-Shiong et al. | 522/26 |
| 5,846,530 A | * | 12/1998 | Soon-Shiong et al. | 424/93.7 |

FOREIGN PATENT DOCUMENTS

| WO | 93/09176 | * 5/1993 |
|---|---|---|
| WO | WO 94/18954 | 9/1994 |

OTHER PUBLICATIONS

Abuchowski et al., "Alteration of Immunological Properties of Bovine Serum Albumin by Covalent Attachment of Polythylene Glycol" *Journal of Biological Chemistry* 252:3578–3581 (1977).

Benslimane et al., "Degradability of Crosslinked Albumin as an Arterial Polyester Prosthesis Coating in in vitro and in vivo Rat Studies" *Biomaterials* 7:268–272 (1986).

Bernatowicz and Matsueda, "Preparation of Pepide–Protein Immunogens Using N–Succinimidyl Bromoacetate as a Heterobifunctional Crosslinking Reagent" *Anal. Biochem.* 155:95–102 (1986).

Desai and Hubbell, "Tissue Response to Intraperitoneal Implants of Polyethylene Oxide–modified Polyethylene Terephthalate" *Biomaterials* 13:505–510 (1992).

Hansson and Purcell, "Sites that Bind Polymerized Albumin on Hepatitis B Surface Antigen Particles: Detection by Radioimmunoassay" *Infection and Immunity* 26:125–130 (1979).

Imai et al., "A Receptor for Polymerized Human and Chimpanzee Albumins on Hepatitis B Virus Particles Co–occuring with HBeAg" *Gastroenterology* 76:242–247 (1979).

Konstan et al., "Effect of High–Dose Ibuprofen in Patients with Cystic Fibrosis" *New England Journal of Medicine* 332:848–854 (1995).

(List continued on next page.)

Primary Examiner—Jeffrey E. Russel
(74) Attorney, Agent, or Firm—Stephen E. Reiter; Foley & Reiter

(57) ABSTRACT

In accordance with the present invention, there are provided rapidly crosslinkable polypeptides which are obtained upon introduction of unsaturated group(s) into the polypeptide via linkage to amino acid residues on the polypeptide directly through one of three types of linkages, namely, an amide linkage, an ester linkage, or a thioester linkage. Each of these linkages are obtainable in a single step by use of a single derivatizing agent, acrylic anhydride. Also provided are methods for preparing such modified polypeptides and various uses therefor. It has unexpectedly been found that proteins with the above-described chemical modifications have the ability to rapidly crosslink to themselves under suitable conditions. This crosslinking occurs in the absence of any external crosslinking agents (indeed, in the absence of any extraneous agents), resulting in the formation of a solid gel material. Solid crosslinked gels are formed in seconds, starting from a freely flowing solution of polypeptide. Applications of such materials are broad ranging, including the encapsulation of living cells, the encapsulation of biologically active materials, the in situ formation of degradable gels, the formation of wound dressings, the prevention of post-surgical adhesions, gene delivery, drug targetting, as a microcarrier for culture of living cells, and the like.

18 Claims, No Drawings

OTHER PUBLICATIONS

Langhein and Newman, "Antibody Response to Bacterial Antigens Covalently Bound to Biodegradable Polymerized Serm Albumin Beads" *J. Applied Bacteriology* 63:443–448 (1987).

Law et al., "Effect of Stabilization Temperature on the Degradation of Adriamycin in Albumin Bicrospheres" *Biomat., Art. Cells & Immob. Biotech.* 19:613–629 (1991).

Lee et al., "Antibodies to Polymerized Human Serum Albumin in Acute and Chronic Liver Disease" *Hepatology* 7:906–912 (1987).

Michalak and Bolger, "Characterization of the Binding Sites for Glutaraldehyde–Polymerized Albumin on Purified Woodchuck Hepatocyte Plasma Membranes" *Gastroenterolgoy* 96:153–166 (1989).

Park, K., "Enzyme–Digestible Swelling Hydrogels as Platforms for Long–Term Oral Drug Delivery:Synthesis and Characterization" *Biomaterials* 9:435–441 (1988).

Soon–Shiong et al., "Islet Purification by a Novel Immunomicrosphere Cell Depletion Technique" *Transplantation Proceedings* 22:780–781 (1990).

Trevisan et al., "Demonstration of Albumin Receptors on Isolated Human Hepatocytes by Light and Scanning Electron Microscopy" *Hepatology* 2:832–835 (1982).

Welz and Ofner, "Examination of Self–Crosslinked Gelatin as a Hydrogel for Controlled Release" *Journal of Pharmaceutical Sciences* 81:85–90 (1992).

Yan et al., "Functional Properties of Proteins Immobilized on Albumin Microspheres" *Biotechnology and Applied Biochemistry* 10:13–20 (1988).

* cited by examiner

CROSSLINKABLE POLYPEPTIDE COMPOSITIONS

FIELD OF THE INVENTION

The present invention relates to methods for the modification of polypeptides. In a particular aspect, the present invention relates to modified polypeptides which can readily be crosslinked to produce a gel under extremely mild conditions. Such materials can be used, for example, for encapsulation of biologically active materials, including living cells.

BACKGROUND OF THE INVENTION

The crosslinking of proteins by various means has generated much interest in the fields of drug delivery, protein immobilization, enzyme and antibody immobilization, peptide-protein conjugation, vaccines, medical imaging, etc. The applications of such crosslinked protein systems are as diverse as the methods employed to achieve crosslinking.

The use of crosslinked proteins as scaffolds for drug delivery has been pursued by several investigators due to the intrinsic biodegradable nature of proteins in vivo. By far the most common method for protein crosslinking is the addition of external crosslinking agents.

Crosslinked protein compositions may take several forms. Microspheres comprising crosslinked proteins are typical in applications that involve drug delivery. Microspheres of proteins are typically prepared by emulsification of an aqueous protein solution with an organic phase and crosslinking by addition of multifunctional crosslinking agents such as glutaraldehyde (Langhein et al., 1987, J. Appl. Bacteriology 63: 443–448; Yan et al., 1988, Biotechnology and Applied Biochemistry 10: 13–20), or by heat denaturation (Law et al., 1991, Biomat. Art. Cells & Immob. Biotech. 19:613–629; Welz and Ofner, 1992, J. Pharmaceutical Sciences 81:85–90).

Immobilization of proteins on surfaces for enzymatic and chromatographic applications has also been reported in the literature. Proteins and peptides may be immobilized at surfaces by use of crosslinking agents such as glutaradehyde and carbodiimides (Benslimane et al., 1986, Biomaterials 7:268–72). Preparation of protein-protein or protein-peptide conjugates is commonly performed by use of glutaraldehyde as well as by use of heterobifunctional crosslinking agents such as N-succinimidyl bromoacetate (Bernatowitz and Matsueda, 1986, Anal. Biochem. 155: 95–102). Proteins have also been modified to introduce functional groups that may be polymerized upon exposure to free radicals resulting in the formation of crosslinked hydrogels (Park, 1988, Biomaterials 9:435–441).

Although most of the methods referred to above result in the formation of crosslinked proteins, the use of external agents (and the reaction conditions required for crosslinking) are too toxic for such processes to be carried out in the presence of living cells and tissues. Indeed none of the references noted above teach their respective art in the presence of living systems.

It is well known that agents of crosslinking such as those described above are in fact used as fixatives for cells and tissues. In a slightly different approach from the addition of external crosslinking agents, Park (1988), supra, describes the free radical polymerization of monomers such as acrylic acid and acrylamide along with derivatized proteins as multifunctional crosslinkers for the formation of polyacrylic acid and polyacrylamide gels. In this case the protein, derivatized with unsaturated groups capable of undergoing free radical polymerization, serves merely as the crosslinker, while the bulk of the resultant hydrogel is either polyacrylic acid or polyacrylamide. The formation of crosslinked hydrogels also necessitates the use of toxic free radical initiators, such as ammonium persulfate, and polymerization conditions that involve teperatures of 60° C. as well as polymerization times of an hour or more. No known living cells, except thermophilic organisms, are likely to survive such crosslinking conditions. Thus, in general, the encapsulation of living cells in a crosslinked protein gel has not been described in the art.

In general the encapsulation of cells requires conditions that are particularly fastidious with respect to mild temperatures,. absence of toxic chemicals, rigid maintainence of physiological conditions of pH and osmolarity, and processes that in general are fairly rapid so as to minimize the exposure of the living cells to adverse conditions. A good example of a nontoxic encapsulation process is the one using sodium alginate (a polysaccharide) that can be formulated in physiological saline (see, for example, Soon-Shiong et al., 1991, Transplantation Proceedings 23:758). Cells are simply suspended in a solution of polysaccharide, which is added dropwise into a solution of calcium chloride, resulting in the instantaneous formation of capsules of ionically crosslinked alginate containing entrapped cells.

Since proteins, in general, do not spontaneously form gels, external agents must be added to facilitate the formation of crosslinked hydrogels (an exception is gelatin, which can coagulate to form a gel below a certain temperature). The resulting protein hydrogels could potentially be utilized to entrap cells in a crosslinked protein matrix. Thus the solution of a protein may be stirred with an added external crosslinking agent to form a crosslinked protein mass or gel. Alternately the formation of a protein gel in the form of spheres or microspheres requires emulsification with a non-solvent phase to form discrete droplets of the protein solution which can subsequently be crosslinked. However, as described above, common processes utilized to crosslink proteins suffer from the limitations of toxicity when contemplated for the encapsulation of living material.

There are several advantages attendant to the use of proteins as encapsulation materials for living cells and tissue. Proteins such as albumin, collagen, gelatin, and the like, being of natural origin, are well tolerated by living cells. For example, the use of albumin in culture media is well known and is in fact essential for the well being of cell cultures. Collagen is secreted by cells and forms the major component of the extracellular matrix. Gelatin is known to support cell adhesive behavior through its binding with fibronectin, another ubiquitous cell adhesion molecule. Thus a matrix of such proteins in the form of a microcapsule is favorable for the growth of the encapsulated cell. In fact commercially available gels such as Matrigel and Atrigel, both of which contain collagen, are known for their ability to support viable cells.

Albumin is considered to be an 'inert' protein since it does not bear epitopes that play a role in cell adhesion under normal physiological conditions. As a result, it does not support cell adhesion and is often utilized as a coating in applications that require a cell-free surface. Thus microcapsules or crosslinked gels of albumin are not expected to show a cell adhesive response when transplanted into a host organism. This effect in general is termed as 'biocompatibilty'. Thus in applications such as cell therapy where foreign cells are encapsulated and transplanted to replace lost function in the host, such a 'coating' or encapsulation of the transplanted cell would prevent an inflammatory and fibrous reaction to the transplanted material. On the other hand, it is often required that transplanted tissue become vascularized or that the material of encapsulation become vascularized so that the encapsulated cells within the matrix of the crosslinked material are in reasonable proximity to a source of nutrients, and, more importantly, to a source of oxygen. In such a case, the use of crosslinked collagen or gelatin would be of great benefit in supporting the growth of vascularized tissue adjacent to the encapsulated cell.

Thus, it is essential to develop protein compositions and processes that can result in the formation of crosslinked protein gels in the presence of living cells in a manner that is innocuous to the well being of the cellular material. The essential requirements of such compositions and processes would be as follows:

the ability to crosslink in the presence of a suitable initiating system, where the initiating system itself is nontoxic;

the protein composition should be nontoxic;

the crosslinking reaction must be nondetrimental to the cellular material, i.e, it produces little or no heat, it produces no by-products that are harmful to the living material and it does not alter, by chemical reaction, the chemical nature of the encapsulated material; and the process must be extremely rapid (it should be complete in a timescale measured in seconds) to avoid prolonged exposure of the encapsulated material to the crosslinking conditions.

The present invention discloses compositions and processes that satisfy each of the above stringent requirements.

In general, the production of crosslinked hydrogels requires the use of water-soluble monomers or macromonomers (in the case where the starting soluble material is a polymer that is subsequently crosslinked) These monomers or macromonomers are dissolved in aqueous medium and suitable agents are added to initiate crosslinking. Crosslinking of proteins is conventionally carried out with addition of crosslinking agents such as those mentioned above. Alternately, the monomers and macromonomers may possess functional groups that are themselves capable of undergoing a crosslinking reaction, without the addition of external crosslinking agents, when subjected to the appropriate conditions. A typical example is the formation of a polyacrylamide gel. The monomer, acrylamide, along with a small amount of bis-acrylamide, is dissolved in an aqueous phase. In the presence of a free radical initiating system, this mixture yields a polymerized crosslinked gel. Another example is the use of a macromonomer, such as polyethylene glycol diacrylate (which is a polyethylene glycol with two introduced acrylate functionalities), which may be dissolved in an aqueous phase. In the presence of free radicals, the acrylate groups polymerize, resulting in a crosslinked hydrogel.

The case of proteins, however, presents special problems. The introduction of a free radical polymerizable group (a functional group containing a polymerizable double or triple bond, also known as unsaturation) into the protein molecule is not trivial due to the sensitivity of the protein to its environment. The use of organic solvents and other harsh conditions commonly used to modify synthetic polymers are not possible with proteins due to their denaturation potential. For example, in the synthesis of polyethylene glycol diacrylate (PEG-DA) from PEG, one can use the derivatizing reagent acryloyl chloride. This reagent is extremely reactive and results in excellent yield of PEG-DA in a dry organic solvent such as dichloromethane or benzene. However, the presence of moisture will rapidly destroy the derivatizing capability of this reagent due to its rapid reaction with water. Such a reagent is clearly unacceptable for modification of protein, given that most proteins will not tolerate organic solvents.

Although it has been reported in the art that a functional group containing unsaturation may be introduced into a protein molecule under relatively mild aqueous conditions, we have found in the course of the present work that this in itself is not a necessary and sufficient condition for the rapid (within seconds) formation of a crosslinked protein gel.

BRIEF DESCRIPTION OF THE INVENTION

In accordance with the present invention, we have discovered that a rapidly crosslinkable polypeptide may be obtained if, and only if, the unsaturated group introduced into the polypeptide is linked to amino acid residues on the polypeptide directly through one of three types of linkages, namely, an amide linkage, an ester linkage, or a thioester linkage. In addition, each of these linkages are obtainable in a single step by use of a single derivatizing agent, acrylic anhydride.

It has unexpectedly been found that proteins with the above-described chemical modifications have the ability to rapidly crosslink to themselves under suitable conditions. This crosslinking occurs in the absence of any external crosslinking agents (indeed, in the absence of any extraneous agents), resulting in the formation of a solid gel material. Solid crosslinked gels are formed in seconds, starting from a freely flowing solution of polypeptide. Applications of such materials are broad ranging, including the encapsulation of living cells, the encapsulation of biologically active materials, the in situ formation of degradable gels, the formation of wound dressings, the prevention of post-surgical adhesions, gene delivery, drug targetting, as a microcarrier for culture of living cells, and the like.

DETAILED DESCRIPTION OF THE INVENTION

In accordance with the present invention, there are provided chemically modified polypeptides having the formula:

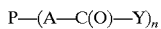

P—(A—C(O)—Y)$_n$ wherein:
P is any polypeptide,
A is a linking moiety which, in combination with a carbonyl moiety, links Y to P,
Y is an unsaturated group capable of undergoing free radical polymerization, and
n is at least 1.

Virtually any polypeptide can be used in the practice of the present invention, including naturally occurring polypeptides, synthetic polypeptides, short chain peptides having only a few residues, extremely high molecular weight polypeptides, and the like.

The linking moiety "A" employed in the practice of the present invention to link unsaturated group, Y (via a carbonyl) to polypeptide P is typically derived from a reactive residue on the polypeptide backbone. Thus, A is generally selected from —O—, —S—, —NR— or alkylene, or an —O—, —S— or —NR—containing alkylene moiety, wherein R is selected from hydrogen or lower alkyl.

Y of the above formula can be any alkene-containing moiety or alkyne-containing moiety, with terminal unsaturation preferred because such species are more reactive than internally unsubstituted compounds. Thus, a preferred group of species which are contemplated for use in the practice of the present invention are defined as follows:

$$-C(R)=CR'_2,$$

or $$-C\equiv CR'$$

wherein:

R is selected from hydrogen, lower alkyl or substituted lower alkyl, and

R' is selected from hydrogen or lower alkyl.

It is preferred that each R' in the above formulae is hydrogen, with Y being —CH=CH$_2$ or —C≡CH preferred.

The degree of substitution on polypeptide, P, can vary widely. Typically, n of the above general formula falls in the range of 1 up to about 500, with n in the range of about 2–300 preferred; and n in the range of about 3–100 especially preferred. For many medium sized proteins, n can fall in as narrow a range as 5 up to about 60. Of course, those of skill in the art recognize that the desired level of substitution will vary depending on the ultimate use contemplated.

The present invention is based on the observation that polypeptides substituted with unsaturated groups linked to amino acid residues in the polypeptide only through very specific linkages, have the capability of rapidly polymerizing under appropriate free radical initiating conditions to form crosslinked polypeptide gels. More specifically, the invention is based on the ability to very rapidly (in seconds) form crosslinked gels from modified polypeptides starting from a freely flowing solution of polypeptide. Thus, by exposing a polypeptide solution to a suitable wavelength of light (visible or ultraviolet) in the presence of the appropriate photoinitiators and catalysts, rapid formation of crosslinked gels occurs.

Invention compositions comprise naturally occurring or synthetic polypeptides modified by the substitution of an unsaturated group linked through an amide, ester or thioester linkage to the amines, hydroxyls or sulfhydryl groups, respectively, present on the amino acid residues on the polypeptide. The invention is premised, at least in part, on the unexpected observation that the introduction of a plurality of unsaturated groups into a polypeptide molecule is not the necessary and sufficent condition for rapid formation of a crosslinked gel upon exposure of the polypeptide solution to photoinitiating conditions. In accordance with the present invention, it has been discovered that it is how these unsaturated groups are linked to amino acids (i.e., the particular intervening chemical linkages between the unsaturated groups and the amino acid residues) in the protein that determines the rapidly crosslinkable nature of the resulting substituted protein molecules.

For example, a protein reacted with glycidyl acrylate in aqueous conditions results in vinyl (—CH=CH$_2$) substituents, but these vinyls are linked to the protein through intervening groups {CH$_2$—CH(OH)—O—CO}, as indicated below:

Reaction at lysine residues:

Protein-NH—{CH$_2$—CH(OH)—O—CO}—CH=CH$_2$     (1a)

Reaction at serine residues:

Protein-O—{CH$_2$—CH(OH)—O—CO}—CH=CH$_2$     (1b)

Reaction at cysteine residues:

Protein-S—{CH$_2$—CH(OH)—O—CO}—CH=CH$_2$     (1c)

If a solution of the above modified protein with a plurality of such substitutents is exposed to conditions of photoinitiated free radical formation, it will not rapidly crosslink to form a coherent gel.

Another example of the introduction of vinyl substituents into a protein molecule is the reaction of protein with allyl bromide in aqueous media. This results in the following derivative of the protein, in which the intervening group between the vinyl and the amino acid is {CH$_2$}:

Reaction at lysine residues:

Protein-NH—{CH$_2$}—CH=CH$_2$     (2a)

Reaction at serine residues:

Protein-O—{CH$_2$}—CH=CH$_2$     (2b)

Reaction at cysteine residues:

Protein-S—{CH$_2$}—CH=CH$_2$     (2c)

If a solution of the above modified protein with a plurality of such substitutents is exposed to conditions of photoinitiated free radical formation, it will not rapidly crosslink to form a coherent gel.

However, if a protein or polypeptide is reacted with acrylic anhydride in aqueous media to obtain the following vinyl containing structures, in which the intervening group is {CO}:

Reaction at lysine residues:

Protein-NH—{CO}—CH=CH$_2$     (3a)

Reaction at serine residues:

Protein-O—{CO}—CH=CH$_2$     (3b)

Reaction at cysteine residues:

Protein-S—{CO}—CH=CH$_2$     (3c)

it is found that such a protein or polypeptide, having an equivalent degree of substitution of vinyl groups as in the two examples set forth above will rapidly crosslink (in seconds), resulting in the formation of a coherent gel.

The potential amino acids that are likely to be derivatized by this chemistry are those containing primary or secondary amines (—NH$_2$ or —NHR, respectively; e.g., lysine, proline, tryptophan, asparagine, glutamine, arginine, histidine), those amino acids containing primary or secondary hydroxyls (—OH; e.g., serine, threonine, tyrosine), and those amino acids containing sulfhydryls (—SH; cysteine). In each of the above cases, due to the reactivity of the reagents with nucleophiles in general, a small fraction of the vinylic substitution occurs on amino acid residues containing hydroxyl groups and sulfhydryl groups. However, due to the general preponderence of lysines (relative to serine and cysteine residues) in proteins, most of the vinylic substitution on the protein is expected to occur at the lysine residues. In addition, glycosylated proteins possessing sugar residues or carbohydrate moieties will also be derivatized due to the reactivity of acrylic anhydride with nucleophiles in general.

The latter examples of vinylic substitution (structures 3a, b, c) provide a great unexpected advantage due to the rapid crosslinking capability of the substituents resulting from the reaction of the protein with acrylic anhydride. In other words, a solution of the modified protein of structure 3 when subject to the appropriate photoinitiating conditions, can polymerize in a matter of seconds to a homogeneous crosslinked protein gel.

However, in the cases of modified proteins (or polypeptides) of structures 1 and 2 above, under the same conditions of photoinitiation, protein concentration etc., the reaction does not progress rapidly enough to form a crosslinked protein gel in similar time frames. External monomers such as acrylic acid or acrylamide may be added in such cases (i.e., for proteins 1 and 2) to cause such a solution to polymerize and form a gel. In such a case, the high reactivity and rapid polymerizing ability of these monomers overrides the lower reactivity of the unsaturated substituents on the proteins (in case of proteins 1 and 2) and in a sense 'kick starts' the reaction to completion. These monomers, however, have to be present at relatively high concentrations for such a reaction to occur (typically greater than 10% by weight of solution). Moreover the severe toxicity of these monomers and large exotherms produced under rapid photoinitiating conditions proves lethal in the presence of living cells and tissue. A good example is the polymerization of cyanoacrylates on tissue, which is well known to cause tissue necrosis.

Thus the present invention describes protein and polypeptide compositions (structures 3 a, b, c) containing unsaturated groups linked directly to amino acid residues in the protein through a {CO} group. These linkages can occur on any amino acid residues that possess primary or secondary amine (e.g., lysines), primary or secondary hydroxyl (e.g., serines) or sulfhydryl (e.g., cysteines) groups. These modified proteins in solution form have the capability to rapidly (within seconds) form a crosslinked protein gel under conditions of photoinitiated free radical generation with no toxicity to living cells or tissue and without the addition of substantial quantities of non-protein free radical polymerizable monomers.

In accordance with one aspect of the present invention, a technique for modification of polypeptides in an aqueous environment that does not result in any adverse effects on polypeptide structure has been developed. Thus, in accordance with the present invention, there is provided a method for preparing chemically modified polypeptides capable of undergoing free radical polymerization. The invention method comprises:

contacting a polypeptide, P, with a reactant containing the group —C(O)—Y, wherein Y is an unsaturated group capable of undergoing free radical polymerization, and wherein said contacting is carried out under conditions suitable to link the moiety —C(O)—Y to P.

The use of the reagent acrylic anhydride as the functionalizing reactant results in substituted proteins that can readily be polymerized under the appropriate free radical generating conditions. Other agents such as allyl bromide or glycidyl acrylate that can also be utilized to functionalize proteins in an aqueous environment do not result in a protein that can rapidly crosslink to form a gel. While not wishing to be bound by any theory, it is presently believed that this most probably arises from the effect of the chemical group immediately adjacent to the vinyl group, i.e., it is the nature of the intervening linkage between the vinyl group and the nucleophilic group on the amino acid that determines the reactivity of the vinyl group in the presence of free radicals. In accordance with the present invention, it has unexpectedly been found that when this linkage is a carbonyl group, i.e., —{CO}—, the reactivity of unsaturated groups to free radicals is greatly enhanced as compared to the cases where groups such as —{CH$_2$}— or —{CH$_2$—CH(OH)—O—CO}— serve as the intervening linkages. The reagent acrylic anhydride, when reacted with typical nucleophiles in the protein, provides an intervening group between unsaturated groups and the amino acid that is a —{CO}— linkage. Other reagents which also provide the desired intervening group between unsaturated groups and the amino acid include alkenoic acids or the corresponding acid halides or acid anhydrides thereof, alkylol (meth)acrylamide derivatives, and the like. Presently preferred reactants are alkenoic acid anhydrides. Exemplary reactants include acryloyl chloride, methacryloyl chloride, acrylic acid, methacrylic acid, acrylic anhydride, methacrylic anhydride, N-methylol acrylamide, N-methylol methacrylamide, and the like.

Any protein that possesses sufficient quantities of nucleophile-containing amino acids can be reacted with acrylic anhydride to produce a rapidly photocrosslinkable material. Most proteins have several lysine residues in the structures that are accessible to modification by this technique. For example, proteins such as albumin, collagen, gelatin, immunoglobulins, hemoglobin, transferrin, caesin, pepsin, trypsin, chymotrypsin, fibronectin, vitronectin, laminin, lipase, hemoglobin, lysozyme, fibrinogen, transferrin, interleukin-1, interleukin-2, tissue necrosis factor, colony-stimulating factor, epidermal growth factor, transforming growth factors, fibroblast growth factor, insulin-like growth factors, hirudin, tissue plasminogen activator, urokinase, streptokinase, erythropoietin, Factor VIII, Factor IX, insulin, somatostatin, proinsulin, macrophage-inhibiting factor, macrophage-activating factor, muramyl dipeptide, interferons, glucocerebrosidase, calcitonin, oxytocin, growth hormone, α-1 antitrypsin, superoxide dismutase, α-2-macroglobulin, lactalbumin, ovalalbumin, amylase, and the like.

In addition to the above-described proteins, polypeptides as short as a few residues (e.g., RGD, YIGSR (SEQ ID NO:1), REDV (SEQ ID NO:2), PDSGR (SEQ ID NO:3), IKVAV (SEQ ID NO:4), RDGF (SEQ ID NO:5), GRGD (SEQ ID NO:6), RGDY (SEQ ID NO:7), GRGDY (SEQ ID NO:8), GYIGSR (SEQ ID NO:9), GYIGSRY (SEQ ID NO:10), RGDS (SEQ ID NO:11), GREDV (SEQ ID NO:12), GREDVY (SEQ ID NO:13), GRGDF (SEQ ID NO:14), GPDSGR (SEQ ID NO:15), GPDSGRY (SEQ ID NO:16), GIKVAV (SEQ ID NO:17), IKVAVY (SEQ ID NO:18), GIKVAVY (SEQ ID NO:19), and the like) can also be treated in accordance with the present invention. Such polypeptides can be chemically modified by the methods described herein, as well as entrapped within a crosslinked gel of a modified peptide.

The degree of substitution on the protein or polypeptide treated as described herein can be varied quite easily by using varying molar ratios of acrylic anhydride to the protein/polypeptide (or to the lysines in the protein/polypeptide). Lower substitution results in softer gel formation following the crosslinking reaction compared to proteins with higher degrees of substitution. The former gels are more diffusible that the latter. Thus, adjustment of the degree of substitution allows for the synthesis of a range of materials having from highly diffusible to poorly diffusible crosslinked matrices. The variation of degree of substitution also dictates the rates of in vivo degradation of the crosslinked gels. Thus the degradation rate of the material can be tailored to the requirements of the contemplated applications, i.e., short or long degradation times can readily be achieved. Furthermore, the diffusibility of the crosslinked matrix may be tailored to applications such as drug delivery, cell encapsulation, etc.

The photocrosslinking or photopolymerization of modified proteins and/or polypeptides obtained by the modification reaction described herein is performed in the presence of free radical initiating system (e.g., a photosensitizing agent and optionally, a cocatalyst). Typical free radical producing conditions include exposure of the materials to be crosslinked to visible or ultra-violet light. Appropriate photoinitiators and light sources for use can be readily identified by those of skill in the art. In the case of visible light, photoinitiators (also known as photosensitizer or dye) such as ethyl eosin, eosin, erythrosin, rose bengal, thionine, methylene blue, riboflavin may be used. Most visible light photoinitiators require the presence of a cocatalyst (also known as cosynergist, activator, initiating intermediate, quenching partner) to generate the free radicals necessary for polymerization of unsaturated substituents. Examples of such cocatalysts are triethanol amine, methyl diethanol amine, triethylamine, arginine, and the like. Optionally, the addition of a small quantity of a comonomer (e.g., 1-vinyl 2-pyrrolidinone, acrylamide, methacrylamide, acrylic acid, methacrylic acid, sodium acrylate, sodium methacrylate, hydroxyethyl acrylate, hydroxyethyl methacrylate (HEMA), ethylene glycol diacrylate, ethylene glycol dimethacrylate, pentaerythritol triacrylate, pentaerythritol trimethacrylate, trimethylol propane triacrylate, trimethylol propane trimethacrylate, tripropylene glycol diacrylate, tripropylene glycol dimethacrylate, glyceryl acrylate, glyceryl methacrylate, and the like) can aid in increasing the overall rate of the polymerization reaction. In the case of UV light, photoinitiators that absorb in the UV range such as 2,2-dimethyl phenoxyacetophenone, other acetophenones, benzophenones and their ionic derivatives (for water solubility), benzils and ionic derivatives, thioxanthones and ionic derivatives, and the like, may be utilized.

In accordance with a particular aspect of the present invention, there are provided articles comprising crosslinked, chemically modified polypeptides as described herein having biologically active material entrapped therein. A wide range of biologically active materials are contemplated for use herein, including peptides, proteins, enzymes, hormones, cytokines, nucleic acids, drugs, and the like. Not only can the chemically modified polypeptides described herein be employed to entrap biologically active material therein, in addition, the polypeptide employed for encapsulation can itself impart physiological activity to the resulting article.

The application of such rapidly crosslinkable polymers is clearly multifold, ranging from the use in encapsulation of cells, microcarrier cultures, drug delivery from a biodegradable scaffold, targeted delivery of drugs, genes, vaccines, and the like, the prevention of post surgical adhesions, a scaffold for artificial skin, etc. Some of these applications are outlined below.

The rapidly crosslinkable nature of the modified proteins/polypeptides of the invention allow for the formation of crosslinked gels within seconds of exposure to appropriate photoinitiating conditions. The nontoxic nature of the crosslinking reaction allows for entrapment of living cells in the crosslinked matrix. Such a crosslinked matrix may take several geometrical forms such as spheres, sheets, blocks, cylinders, disks, etc., depending on the end use contemplated. The viability of cells under such crosslinking conditions has clearly been demonstrated in the course of the present work.

The crosslinking of proteins (or polypeptides) in the presence of living cells, without toxicity thereto, has not been previously demonstrated in the art. Typical emulsification processes can be utilized in conjunction with the modification processes described herein to generate microspheres in the submicron size range. Photopolymerization of the resulting submicron particles produces submicron particles of crosslinked proteins and/or polypeptides. Such microparticles have applications in a wide variety of fields, e.g., in drug delivery, gene therapy, diagnostic imaging, and the like. In a specific aspect, microspheres prepared under controlled low shear conditions can be utilized for cell encapsulation. Such microspheres may be a few microns to several hundred microns, depending on the cell types encapsulated.

For example, hepatocytes encapsulated in photocrosslinked albumin microspheres can be used as a detoxification system for patients in liver failure. Thus, plasma from the patient is perfused over a bed of encapsulated hepatocytes in order to detoxify or metabolize the accumulated toxins in the patient's blood. In addition, in the case of liver failure, activated carbon (or charcoal), which is commonly used as an adsorbent for toxins, may also be entrapped in a matrix of crosslinked peptides, such as albumin, and used in a similar fashion.

In addition to entrapment of living cells within a crosslinked protein (or polypeptide) matrix, microspheres of crosslinked protein (or polypeptide) may be utlilized as a substrate for cell growth. Thus the culture of living cells on microcarriers comprising a crosslinked protein (or polypeptide) matrix is possible. For example, the use of photocrosslinked gelatin beads in the size range of a few microns to several hundred microns may effectively be utilized as a support for living cells such as hepatocytes. Gelatin is known to support cell adhesion on the basis of its affinity for fibronectin, a cell adhesion molecule.

The use of crosslinked albumin beads as cell growth subsrates also provides some interesting opportunities. In general albumin is considered a relatively non-adhesive protein. In fact, several groups have demonstrated that coating of surfaces with albumin prevents cell adhesion. This effect could be utilized to advantage in the case where ligand specificity to cell adhesion is to be elucidated. In such a case, a cell non-adhesive substrate is required upon which can be introduced a ligand with specific interactions for the cell type. Thus in the case where the cell would normally not adhere to an albumin substrate, the specific ligand introduced promotes cell interaction with the modified surface. Albumin microcapsules may be easily modified with such ligands to test specific cell-surface interactions.

The immobilization or entrapment of drugs within matrices of crosslinked proteins (or polypeptides) has several applications in the field of drug delivery. In accordance with the present invention, the release profile of drugs from a crosslinked protein (or polypeptide) matrix may be varied by adjusting a number of parameters. Such parameters include the degree of substitution of the protein with unsaturated groups, the concentration of the protein, the loading of the drug, and the like. In addition, the rate of degradation of the protein matrix would also dictate the profile of the released drug. Thus a number of parameters may be manipulated to achieve a desired release profile of a drug.

Microcapsules of crosslinked protein (or polypeptide) with diameters less than 5 microns are suitable for intravenous injection. Such microcapsules containing an entrapped drug can be utilized for intravascular drug delivery. It is known that particulates injected into the blood stream in the micron and submicron size range are scavenged by the reticulo-endothelial system (RES) of cells in the liver and spleen. Crosslinked protein (or polypeptide) microcapsules according to the present invention, containing entrapped drug, will be taken up in these organs and degraded, allowing release of the entrapped drug. Thus, the degradation of these capsules over time should result in a sustained release profile for the encapsulated drug. Several drugs may be contemplated as being useful for delivery in a matrix of crosslinked protein (or polypeptide). Examples of such drugs include analgesic agents (e.g., acetominophen, aspirin, ibuprofen, morphine and derivatives thereof, and the like), anti-asthmatic agents (e.g., azelastine, ketotifen, traxanox, and the like), antibiotics (e.g., neomycin, streptomycin, chloramphenicol, cephalosporin, ampicillin, penicillin, tetracycline, and the like), anti-depressant agents (e.g., nefopam, oxypertine, imipramine, trazadone, and the-like), anti-diabetic agents (e.g., biguanidines, hormones, sulfonylurea derivatives, and the like), anti-fungal agents (e.g., amphotericin B, nystatin, candicidin, and the like), anti-hypertensive agents (e.g., propanolol, propafenone, oxyprenolol, nifedipine, reserpine, and the like), anti-inflammatory agents (e.g., steroidal (e.g., cortisone, hydrocortisone, dexamethasone, prednisolone, prednisone, fluazacort, and the like) and non-steroidal (e.g., indomethacin, ibuprofen, ramifenizone, piroxicam, and the like) agents, anti-neoplastic agents (e.g., adriamycin, cyclophosphamide, actinomycin, bleomycin, duanorubicin, doxorubicin, epirubicin, mitomycin, methotrexate, fluorouracil, carboplatin, carmustine (BCNU), cisplatin, etoposide, interferons, phenesterine, taxol (as used herein, the term "taxol" is intended to include taxol analogs and prodrugs, taxanes, and other taxol-like drugs, e.g., Taxotere, and the like), camptothecin and derivatives thereof (which compounds have great promise for the treatment of colon cancer), vinblastine, vincristine, tamoxifen, and the like, anxiolytic agents (e.g., dantrolene, diazepam, and the like), immunosuppressive agents (e.g., cyclosporine (CsA), azathioprine, mizorobine, FK506, prednisone, and the like), physiologically active gases (e.g., air, oxygen, argon, nitrogen, carbon monoxide, carbon dioxide, helium, xenon, nitrous oxide, nitric oxide, nitrogen dioxide, and the like, as well as combinations of any two or more thereof), as well as other pharmacologically active agents, such as cimetidine, mitotane, visadine, halonitrosoureas, anthracyclines, ellipticine, benzocaine, barbiturates, and the like. In addition, drugs in encapsulated or liposomal form may also be entrapped in a matrix of crosslinked protein.

In addition to encapsulation of drugs, peptides, hormones, proteins, nucleic acid constructs (e.g., IGF-1 encoding sequence, Factor VIII encoding sequence, Factor IX encoding sequence, antisense nucleotide sequences, etc.), enzymatically active agents (e.g., DNAse, ribozymes, and the like), immunostimulating agents (i.e., vaccines, and the like) may be encapsulated or entrapped into the matrix of a polymerized protein (or polypeptide) gel (such as an albumin gel) and injected intravenously (if the particle size is suitable) or administered by subcutaneous or intrathecal injection. The degradable gel is eventually absorbed while the entrapped hormone or peptide is released over time. This possibility has been demonstrated for insulin release over time (see Example 15). Clearly a plethora of such active agents may be delivered by this technique. Any of the above-described compositions are useful for the treatment of disorders which relate to hormone-deficient disease states. Examples of other deliverable agents include agents employed for the treatment of carcinoma, wound healing, erythropoiesis stimulation, stimulation of fibrinolysis, treatment of hemophilia, glucose regulation, immunoregulation, treatment of Gaucher's disease, treatment of bone disease, induction of labor, treatment of dwarfism, treatment of AAT deficiency, treatment of respiratory disorders, and the like.

Crosslinked gels of degradable, non-immunogenic proteins such as albumin, collagen etc. may be injected subcutaneously for cosmetic applications. Injections of collagen are quite commonplace in the field of cosmetic and plastic procedures. The problem with collagen injections is the rapid absorption of the protein after injection. A polymerized/crosslinked gel of collagen or albumin may be injected, and would be expected to degrade over much longer periods of time than do unmodified proteins. Such longer lasting 'implants' may decrease the need for frequent procedures.

In addition to the non-specific uptake of crosslinked protein microspheres by the RES following intravascular administration of these microspheres, specific receptor-ligand interactions between proteins and/or other moieties on the surface of the microspheres and cellular receptors may be exploited for the purpose of targeted delivery of the protein microspheres. An example is the possibility of specific uptake of microspheres into hepatocytes. The presence of a receptor for polymerized human serum albumin (PHSA) on the surface of hepatocytes has been demonstrated by several research groups (Trevisan et al., 1982, Hepatology 2:832–835; Michalak and Bolger, 1989, Gasteroenterology 96:153–66). It has also been established that such a receptor exists on the surface of the hepatitis B virus (HBV) associated with the HBV surface antigen (HBsAg) (Hansson and Purcell, 1979, Infect. Immunol. 26:125–130; Imai et al., Gasteroenterology 1979, 76:242–247). Imai proposed that PHSA may act as a bridge between the virus and the target liver cells thus explaining the restricted host and organ tropism of HBV infection. PHSA, a macromolecule of approximately 400,000 daltons, as well as antibodies to PHSA have been detected in human plasma, particularly in patients with chronic liver diseases (Lee et al., 1987, Hepatology 7:906–912). In normal individuals, the presence of PHSA in the circulation maybe a result of the normal aging process of albumin in human serum, such as excessive oxidation and crosslinking via cysteine residues, and the PHSA receptor on hepatocytes may function as the clearance terminal for PHSA as part of the system for albumin homeostasis in vivo. It has been demonstrated that albumin polymerized with glutaraldehyde can bind to these receptors on the hepatocyte (Michalak and Bolger, 1989), supra.

Without wishing to be bound by any theory, it is proposed, based on the evidence presented herein, that albumin, polymerized and/or crosslinked via unsaturated groups incorporated into the protein molecule, would bind to this receptor on the hepatocyte and serve as a targeting moiety for the delivery of pharmacologically active agents to the hepatocyte when the agents are carried along with the crosslinked albumin. Moreover, exploitation of the binding of PHSA to HBsAg could be utilized to remove significant titers of circulating HBV from blood by contact with a bed of crosslinked albumin particles. In addition, the delivery of genes to hepatocytes for the treatment of genetically deficient states such as hemophilia may be of great benefit. Encapsulation of the genes for Factor VIII production and subsequent delivery directly into the hepatocyte may result in the integration of this gene into the genome of the hepatocyte, resulting in the production of Factor VIII. Several genetically deficient disease states may avail of this methodology employing microcapsule formulations for the delivery of genes to specific sites.

Another example is the delivery of drugs or genetic material to the lungs in an aerosolized formulation.

Crosslinked microspheres of proteins in the 1–5 micron size range would be effective in delivery of entrapped or encapsulated pharmacological agents to the lungs. For example anti-inflammatory agents such as ibuprofen or indomethacin may be inhaled directly into the lungs for the treatment of cystic fibrosis. These drugs have been shown to have significant alleviating effects from the disease (Konstan et al., in New England J. Med., 1995, 848–854).

Another application of rapidly photocrosslinkable proteins (or polypeptides) lies in the prevention of post-operative or post-surgical adhesions. Post-operative adhesions, or filmy connective or scar tissue bridges formed during the normal healing process following surgery, often result in bowel obstructions and infertility arising from kinking of fallopian tubes following abdominal surgery. The isolation of wounded tissue (as a result of surgery) by use of a physical barrier of biocompatible, degradable material between this tissue and the surrounding organs has been shown to alleviate these problems. Viscous solutions of hyaluronic acid (HA, a polysaccharide) have been used previously for this purpose, albeit in a soluble form. As expected, even these fairly viscous solutions of HA are likely to dissolve away, resulting in the eventual formation of adhesions. The use of in situ photocrosslinkable solutions of a protein such as albumin, resulting in the formation of a cohesive gel around the injured tissue, is likely to efficiently isolate the injured tissue from surrounding organs and thus prevent the formation of adhesions. The use of crosslinkable albumin, a protein that does not elicit an adhesive response from cells and is degradable in vivo to harmless by-products, is advantageous over the use of synthetic materials in vivo. Mixtures of photocrosslinkable albumin with hyaluronic acid or a modified photocrosslinkable hyaluronic acid, when polymerized in situ, also serves as a degradable barrier to prevent the formation of adhesions.

The ability to polymerize proteins such as albumin, gelatin, collagen etc. into crosslinked hydrogels extends the possibility of use of these materials into the field of wound dressings and skin substitutes. Crosslinked sheets of these protein hydrogel materials may be used as a substrate for the growth of skin cells such as dermal fibroblasts, keratinocytes, and the like. In general, it is problematic to obtain adhesion of cells to a high water content hydrogel. However, the invention compositions allow for substantial amounts of collagen and/or gelatin to be polymerized and crosslinked directly into the matrix of the crosslinked hydrogel. In addition, unmodified collagen or gelatin may be added to the matrix of the above crosslinked hydrogel to enhance and support cell growth.

Collagen is known to support cell adhesion/anchorage through integrin interactions with cells and gelatin most likely supports cell adhesion through its affinity for fibronectin, a cell adhesion molecule which also interacts with integrin. The required cell types can thereby be cultured on a crosslinked hydrogel matrix sheet containing crosslinked modified albumin, collagen, gelatin etc. in any combination. This sheet of hydrogel and cultured cells may be placed (cell side down) onto wounds such as third degree burns to aid in regeneration of of lost skin. The cells may be taken from the patient for autologous tranplantation to avoid the problems of graft rejection. Allograft and xenograft cells may also be used for this purpose. In addition, the crosslinked hydrogel, being an absorptive matrix, can be loaded with media, nutrients and growth factors essential to the survival of the cultured cells and factors that aid in the proliferation of the patient's skin cells.

Such a crosslinked hydrogel matrix may also be used as a support for the growth of autologous keratinocytes for gene delivery to a topical site. Progenitor or immature basal keratinocytes may be transfected with a gene cultured on the crosslinked hydrogel substrate, then grafted onto the skin. This results in grafted cells that produce a desired gene product in the host. If necessary, at a later time, the cells can be removed by a simple dermal abrasion procedure.

It has been demonstrated that a wound heals faster in the presence of adequate oxygenation than in cases where a lower concentration of oxygen is available to the proliferating cells in the wound bed. In order to make a wound dressing from a crosslinkable protein as described above with a high permeability to oxygen, several approaches may be satisfactory. For example, the addition of a fluorocarbon emulsion into the protein solution followed by polymerization into a hydrogel sheet would increase permeability to oxygen. Microcapsules of hemoglobin that reversibly bind oxygen have been developed (see PCT publication no. WO 94/18954) that could be incroporated into the dressing as a transporter of oxygen to the wound bed. In addition, growth factors, growth stimulants, antibiotic drugs, and the like, can easily be incorporated into the wound dressing during the polymerization phase.

The crosslinked degradable gels of the invention may be used as a scaffold for modelling of tissue growth in vitro or in vivo. For example, a degradable protein gel may be utilized as a scaffold for tissue growth and modelling, e.g., for the formation of leaflets of heart valves. In such case, a suitable cell type is grown on the scaffold to establish a three-dimensional tissue-like morphology while the scaffold degrades over a period of time to generate a tissue structure with the integrity of natural tissue. In addition, these scaffolds may entrap certain factors that promote the growth of particular cell types.

The modified proteins (and/or polypeptides) of the present invention are not limited to photocrosslinking in a solution containing only the modified protein (and/or polypeptide). In general, the modified protein (and/or polypeptide) may be crosslinked in the presence of other monomers, other crosslinkable proteins, other crosslinkable polypeptides, other unmodified proteins, other unmodified polypeptides, other unmodified polymers, and the like. In the case of crosslinking of modified protein (and/or polypeptides) in the presence of other unmodified polymers, entrapment of these polymers within the matrix of the crosslinked protein (and/or polypeptide) is typically achieved. Depending on the molecular weight of the polymer and the degree of substitution of the modified protein, the polymer may be retained within the crosslinked protein matrix if it is large compared to the 'pores' in the crosslinked protein (or polypeptide) matrix, or it may leave the matrix readily by diffusion if its molecular size is smaller than the average 'pore' size of the crosslinked material.

In general, the crosslinking of two or more different materials results in an intimate intermingling of polymer chains and the resultant composition or physical state is often known as an interpenetrating polymer network (IPN). The formation of an IPN of a modified protein with the polysaccharide alginate has been investigated as part of the work described herein. Alginates have been utilized in the encapsulation of living cells and tissue due to their inherent ionically crosslinkable nature. This provides for extremely mild and gentle conditions for encapsulation that are particularly favorable for living systems. Alginate gels crosslinked with multivalent cations such as calcium are particularly porous and easily allow diffusion of large macromolecules through the crosslinked alginate matrix. It is beneficial in certain cases to limit this porosity. By addition of suitable quantities of modified albumin according to the invention to a solution of alginate, followed by ionic crosslinking of the alginate and covalent crosslinking of the albumin by free radical photoinitiation, it is possible to obtain a crosslinked matrix that comprises two components; the alginate ionically crosslinked to itself and the albumin covalently crossslinked to itself. The two polymeric components are now intimately intertwined in the crosslinked state without being chemically linked to each other.

It must also be noted that for a particular protein used in the mixture, only a particular range of compositions (i.e., alginate to Protein ratios) are effective for achieving dual ionic and covalent crosslinking properties. This is because at low protein concentrations (relative to alginate) there is not enough protein present to produce enough crosslinks to stabilize the gel, while at high protein concentrations (relative to alginate), a steric hindrance develops that prevents the alginate from crosslinking (ionically) to itself. Thus an intermediate range or window of concentrations (or ratios) of the two species is required to be determined, for each protein, in order that the resulting mixture will have this dual crosslinking property. Such ratios for alginate and modified albumin have been determined and the resulting solutions utilized for the encapsulation of cells (see Example 20). Any modified protein may be utilized in this method along with any desired polymer, natural or synthetic.

The modified proteins of the invention may also be crosslinked in the presence of other monomers or macromonomers that can undergo free radical polymerization to form crosslinked polymeric materials. For example, modified gelatin may be copolymerized with monomers such as acrylic acid, acrylamide, methacrylamide, methacrylic acid, sodium acrylate, sodium methacrylate, hydroxyethyl acrylate, hydroxyethyl methacrylate, vinyl pyrrolidinone, ethylene glycol diacrylate, ethylene glycol dimethacrylate, pentaerythritol triacrylate, pentaerythritol trimethacrylate, trimethylol propane triacrylate, trimethylol propane trimethacrylate, tripropylene glycol diacrylate, tripropylene glycol dimethacrylate, glyceryl acrylate, glyceryl methacrylate, and the like, to form crosslinked materials. The modified proteins may also be copolymerized with macromonomers such as polyethylene glycol acrylates, polysaccharides substituted with free radical polymerizable groups to generate novel classes of polymeric materials. The advantages of such systems lie in the ability to combine into a single composition, the diverse, unique and advantageous properties of the component materials. An example is the use of alginates in combination with the modified proteins as outlined above.

Another example is the copolymerization of a protein such as modified albumin with polyethylene glycol acrylates to generate microcapsules that are extremely biocompatible, i.e., they resist cellular-cellular adhesion. Polyethylene glycol is well known for its ability to resist protein adsorption and cellular adhesion (Desai and Hubbell, 1992, Biomaterials 13:505). For example, PEG bound to bovine serum albumin has shown reduced immunogenicity and increased circulation times in a rabbit (Abuchowski et al., 1977, J. Biol. Chem. 252:3578). Such microcapsules would show long circulation times in vivo when injected intravascularly and resist uptake by the RES. Applications for such systems would include drug delivery, diagnostic imaging, gene therapy, and the like.

In addition, surfaces of photocrosslinked protein (or polypeptide) microspheres may be modified with suitable ligands such as antibodies, carbohydrate moieties, and the like, that would be recognizable through specific interaction at the receptor level. This would allow for targeting of these crosslinked microspheres.

The invention will now be described in greater detail by reference to the following non-limiting examples.

EXAMPLE 1

Synthesis of Acrylic Anhydride

Acrylic acid (0.2 mol) was reacted with acetanhydride (0.1 mol) at a temperature of 60–70° C. for 2 hours. Finely powdered copper (0.1 g) was added as a polymerization inhibitor. The mixture was then vacuum distilled and three separate fractions collected. The first fraction gave predominantly acetic acid, a reaction product, the second fraction gave a mixture of acetic acid and acrylic acid, and the last fraction with a boiling point of approximately 65° C. at 10 mm Hg was predominantly acrylic anhydride. Purity of the fractions was determined by Fourier Transform Infrared Spectrometry. Yield: 60%.

EXAMPLE 2

Synthesis of a Polymerizable Albumin Derivative

Human Serum Albumin (5 g) was dissolved in 100 ml of water and cooled to 4° C. in an ice bath. Acrylic anhydride (4 ml) was added drop by drop with constant stirring to the cold protein solution and the pH maintained at 9.0 by addition of suitable quantity of 50% NaOH. The stirring was continued for 24 hours at a temperature of 4° C. The reaction product was neutralized and dialyzed against deionized water through a dialysis membrane with a molecular weight cutoff of 12,000–14,000 for 24 hours. The dialysed product was freeze dried to obtain the the protein derivative. Yeild: 3.5 g. The substitution of vinylic groups by this method was targeted to predominantly the lysine amines present in the protein molecule.

General Reaction Scheme

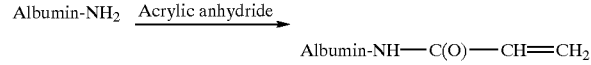

Degrees of substitution may be varied. Small amounts of substitution also occur on amino acids possessing hydroxyl and sulfhydryl groups by the following reactions:

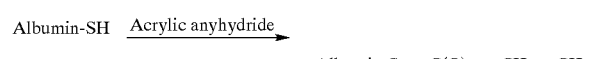

EXAMPLE 3

Synthesis of a Polymerizable Gelatin Derivative

Bovine Gelatin (5 g) was dissolved in 100 ml of water at 40° C. Acrylic anhydride (4 ml) was added drop by drop with constant stirring to the protein solution and the pH maintained at 9.0 by addition of suitable quantity of 50% NaOH. The stirring was continued for 24 hours at a temperature of 40° C. The reaction product was neutralized and dialyzed against deionized water through a dialysis membrane with a molecular weight cutoff of 12000–14000 for 24 hours. The dialysed product was freeze dried to obtain the protein derivative. Yeild: 3.5 g. The substitution of vinylic groups by this method was targeted to predominantly the lysine amines present in the protein molecule.

General Reaction Scheme

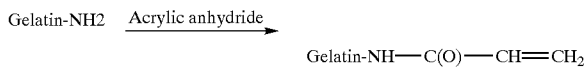

Degrees of substitution may be varied. Small amounts of substitution also occur on amino acids possessing hydroxyl and sulfhydryl groups by the following reactions:

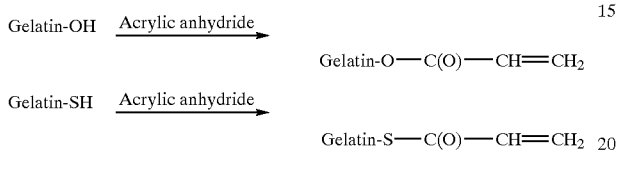

EXAMPLE 4

Laser/Visible Light Photopolymerization to Produce Crosslinked Protein Gels

Substituted proteins prepared by the techniques outlined above were dissolved in aqueous bicarbonate buffered saline (or other buffer) at pH 7.4 at a concentration of 1.0–40% (w/v). A free radical initiating system comprising a dye and a cocatalyst were used to initiate polymerization. The dye, ethyl eosin (0.1 mM to 0.1M), a cocatalyst, triethanolamine (0.1 mM to 0.1M), and optionally, an accelerator (for increasing the rate of polymerization), vinyl pyrrolidinone (0.001 to 10.0%) were added to the solution which was protected from light until the photopolymerization (alternative choices for the initiator, cocatalyst, and wavelength of laser radiation are possible). A small volume of solution was placed in a petri dish and exposed to visible radiation from an argon ion laser at a wavelength of 514 nm at powers between 10 mW to 1W. An exposure time as low as 100 msec was found to be adequate for polymerization. Photopolymerization was also performed with a mercury arc lamp having a fairly strong emission around 514 nm.

EXAMPLE 5

UV Photopolymerization to Produce Crosslinked Protein Gels

A different initiating system from the one in the example above was used to produce protein gels. A UV photoinitiator, 2,2-dimethoxy-2-phenyl acetophenone dissolved in dimethyl sulfoxide, was added to a solution of substituted protein in aqueous buffer at a concentration of 50–5000 ppm. This solution was exposed to long wave UV radiation from a 100 watt UV lamp. The time required for gellation was typically less than 30 seconds although this could vary between 1 and 100 seconds depending on the concentrations of initiator and addition of accelerators such as vinyl pyrrolidinone (0.001 to 10.0%). A UV laser may also be used for the photopolymerization.

EXAMPLE 6

Degree of Modification Measured by Amine Assay

The percentage of lysine amines modified by reaction of the albumin (could be any protein) with acrylic anhydride could be measured by a simple spectrophotometric assay. The free amines in the protein could be titrated against 2,4,6-trinitrobenzene sulphonic acid (TNBS) which shows an increase in absorption at 420 nm upon reaction with a primary amine. Unmodified albumin was utilized as the control and its absorption after reaction with TNBS was measured at 420 nm. The percent of amine groups on the protein substituted by reaction with varying amounts of acrylic anhydride was determined by this assay. Substitution from 0.1% to 99.9% of all amines in the protein was possible as measured by this assay. The table below shows the varying percentages of amine substitution for reactions of acrylic anhydride (AA) with albumin lysines for varying molar ratios of AA to lysines present on the protein:

| AA/Lysine molar ratio | % Lysines Substituted |
|---|---|
| 0.00 | 0.0 |
| 0.43 | 22.2 |
| 3.40 | 66.1 |
| 8.50 | 93.2 |
| 12.80 | 97.6 |

EXAMPLE 7

Comparison of Polymerization Times for Other Vinylic Substituted Proteins

Albumin was reacted with allyl bromide to obtain the structure (2a–c)) shown earlier. Albumin was also reacted with glycidyl acrylate to obtain the structure (1a–c) shown earlier. A solution of 15% (w/v) of these derivatives in water were subject to the polymerization test described in Example 4, in direct comparison with the albumin derivative obtained by reaction with acrylic anhydride. The time required to form a coherent gel in each case was noted. Results are tabulated below:

| Albumin Derivative with: | Polymerization time to coherent gel |
|---|---|
| Glycidyl Acrylate | poor gel > 8 min |
| Allyl Bromide | poor gel > 8 min |
| Acrylic Anhydride | 10 sec |

It can be noted upon review of the results tabulated above that a coherent gel was produced only from the protein that had been modified with acrylic anhydride. Other modifications to the protein that result in the introduction of a vinylic group produced gels that were much softer with very poor consistency and at much longer times.

EXAMPLE 8

Degradation in vivo

Crosslinked albumin gels (synthesized from 25% w/v modified albumin solution) were prepared in the form of cylinders of approximately 5 mm diameter. These were equilibriated with Hanks balanced salt solution (HBSS) for two hours prior to implantation in the peritoneal cavity of mice. The disks were surgically implanted into anesthetized mice by simple incision through the peritoneal wall. The disks were weighed prior to implantation. Mice were sacrificed at 1 week, 2 weeks, 4 weeks and 8 weeks, and the crosslinked protein disks were examined for weight loss due to degradation.

No substantial loss in weight was observed when disks were examined at 1 week and 2 weeks. It was estimated that a 10% and 20% loss in weight had occurred at 4 and 8 weeks, respectively, indicating the degradable nature of the crosslinked gel. By manipulating the concentration of the polypeptide employed for crosslinking, and the degree of crosslinking of the gelled material, the rate of degradation of the crosslinked gel can be varied.

EXAMPLE 9

Preparation of Crosslinked Albumin Microspheres by Emulsification

Human serum albumin modified as above was dissolved in normal saline at a concentration of 10% (w/v). To the solution were added the photoinitiators and accelerators as indicated in the above examples. This solution (1 ml) was added to soybean oil (10 ml) and stirred rapidly using a magnetic stir bar. After 5 minutes of stirring when the protein solution was completely emulsified into the oil, the two phase suspension was exposed to a 100 watt high pressure mercury lamp for 30 seconds to 5 minutes. The protein solution, now as discrete droplets in the oil phase was polymerized into discrete crosslinked gelled spheres of diameter typically less than 100 microns. It was possible to vary this diameter by controlling the shear during emulsification and controlling the emulsification time. Normal saline (5 ml) was added to this emulsion and the tube containing this mixture was centrifuged at 3000×g for 5 minutes. Most of the microspheres produced separated into the aqueous phase. The resulting protein microspheres were stored in saline. Alternate methods of microsphere generation such as spraying, atomization, sonication, electrostatic droplet generation, coextrusion with air or an oil, etc. followed by photocrosslinking will result in stable crosslinked protein spheres.

EXAMPLE 10

Preparation of Crosslinked Gelatin Microspheres by Emulsification

Bovine gelatin, modified as described above (see Example 3), was dissolved in normal saline at a concentration of 5% (w/v). To the solution were added the photoinitiators and accelerators as indicated in the above examples. This solution (1 ml) was added to soybean oil (10 ml) and stirred rapidly using a magnetic stir bar. After 5 minutes of stirring when the protein solution was completely emulsified into the oil, the two phase suspension was exposed to a 100 watt high pressure mercury lamp for 30 seconds to 5 minutes. The protein solution, now as discrete droplets in the oil phase was polymerized into discrete crosslinked gelled spheres of diameter typically less than 50 microns. It was possible to vary this diameter by controlling the shear during emulsification and controlling the emulsification time. Normal saline (5 ml) was added to this emulsion and the tube containing this mixture was centrifuged at 3000×g for 5 minutes. Most of the microspheres produced separated into the aqueous phase. The resulting protein microspheres were stored in saline. Alternate methods of microsphere generation such as spraying, atomization, sonication, electrostatic droplet generation, coextrusion with air or an oil, etc. followed by photocrosslinking will result in stable crosslinked protein spheres.

EXAMPLE 11

Encapsulation of Rat Hepatocytes in Crosslinked Albumin Microspheres

Hepatocytes were isolated from Sprague-Dawley rats by conventional methods of collagenase digestion. The cell pellet (0.2 ml) was resuspended in 1 ml of a solution of 10% modified human serum albumin at physiological pH and osmolarity containing the necessary photoinitiators. This solution was sterile filtered through 0.2 micron filters before use. The cell suspension was added to 10 ml of sterilized soybean oil and gently stirred for 5 minutes before exposure to light as above. Saline was added to the suspension of polymerized albumin droplets containing entrapped hepatocytes and centrifugation at 1000 g for 5 minutes was performed. The encapsulated cells were collected from the aqueous phase and cultured. Viability staining with acridine orange-propidium iodide confirmed the viability of these cells at greater than 90%.

EXAMPLE 12

Microcarrier Culture of Rat Hepatocytes on Crosslinked Gelatin Microspheres

Crosslinked gelatin microspheres of diameter 30–100 microns were prepared as described above (see Examples 3–5). The spheres were sterilized by ethanol exchange prior to culture use. Hepatocytes were isolated from Sprague-Dawley rats by conventional methods of collagenase digestion. The cell pellet (0.2 ml) was added to a 1 ml pellet of gelatin microspheres and the suspension of cells and microspheres cultured initially in static conditions for 4 hours to allow cell attachment to the microspheres and subsequently in roller bottles. After 24 hours the microspheres were observed under the microscope and subtantial adherence of hepatocytes to the gelatin surface was noted. Viability of the cells was greater than 90%.

EXAMPLE 13

Porosity of Crosslinked Protein Gels by Diffusion Studies

FITC-Dextran (3 mg/ml) was dissolved in a solution of modified albumin (25% w/v). Solutions (0.5 ml) with added photocatalysts were taken up into a 1 ml syringe. The syringes were exposed to a high pressure Hg lamp to cause rapid polymerization of the modified albumin resulting in entrappment of the dextrans within the resultant gel. This gel could be sheared through a needle attached to the syringe and a known volume of gelled material could be pushed out of the syringe. Such a system is useful for injection of a gel containing entrapped pharmacological agents to be released upon injection.

Two molecular weights of dextran (4400 daltons and 17500 daltons) were chosen as the probes for porosity determination. Cylindrical gels (0.1 ml) were placed in a tube and Hanks buffer (HBSS) was added to the gels. The gels were incubated in HBSS and the supernantant examined periodically in a spectrophotometer for absorbance at 490 nm. From standard curves of absorbance vs. concentration for the FITC labelled dextran, the amount of dextran diffusing out of the microspheres was determined. By utilizing dextrans of different molecular weights (4.4 kd, 17.5 kd) the relative porosity of the crosslinked hydrogels was estimated. The results are tabulated below:

| Time, hours | % Diffusion, 4kd dextran | % Diffusion, 17.5kd dextran |
| --- | --- | --- |
| 0.016 | 23.6 | 6.4 |
| 0.25 | 30.3 | 11.6 |
| 0.5 | 37.0 | 14.3 |
| 1 | 45.4 | 21.2 |
| 2 | 48.7 | 23.9 |
| 3 | 50.4 | 29.1 |
| 4 | 55.4 | 30.0 |
| 5 | 68.8 | 37.0 |
| 6 | 83.9 | 47.5 |

It is seen, upon inspection of the data the Table, that dextran of molecular weight 4 kd diffuses out of the crosslinked gel faster than the dextran of molecular weight 17.5 kd, as one might expect. Approximately 85% of the 4 kd dextran is released in a 6 hour period in a relatively linear fashion, as compared to ~50% release over the same time period for the 17.5 kd dextran. The 4 kd dextran approximates the molecular size of insulin, and such a release profile is desired for efficient in vivo insulin utilization. See Example 14 for actual experiments with insulin. By altering the concentration of modified albumin in the starting solution, it is possible to alter the porosity of the crosslinked material, thereby altering the relative rate of release.

EXAMPLE 14

In-Vitro Release of Insulin from Crosslinked Albumin Gels

Insulin (Humulin) was dissolved in a solution of modified albumin (25% w/v). Solutions of insulin and modified albumin were made up at concentrations of 5 Units Insulin/ml and 25 Units Insulin/ml each in a 25% albumin solution. The solutions (0.5 ml) with added photocatalysts were taken up into a 1 ml syringe. The syringes were exposed to a high pressure Hg lamp to cause rapid polymerization of the modified albumin resulting in entrappment of the insulin within the resultant gel. This gel could be sheared through a needle attached to the syringe and a known volume of gelled material could be pushed out of the syringe. The gels (0.1 ml) were injected into a tube through a 20G needle and Hanks buffer (HBSS) was added to the gels. The gels were incubated in HBSS and the withdrawn periodically and analyzed for insulin by radioimmunoassay. From standard curves of radioactivity vs. concentration of insulin, the amount of insulin diffusing out of the gels was determined. This information was useful in determining doses for in vivo studies. The results are tabulated below. Clearly, by adjusting the porosity of these gels the release of insulin could be controlled so that a longer or shorter acting insulin may be designed.

| Time (min) | 5 Units/ml Gel % Insulin Released | 25 Units/ml Gel % Insulin Released |
| --- | --- | --- |
| 0 | 0.0 | 0.0 |
| 1 | 5.8 | 3.7 |
| 5 | 14.0 | 37.4 |
| 15 | 23.2 | 47.1 |
| 30 | 30.7 | 50.4 |
| 60 | 31.8 | 51.0 |
| 120 | 37.5 | 53.8 |

EXAMPLE 15

In Vivo Release of Insulin from Crosslinked Albumin Gels

Insulin gels prepared as described above (see Example 14), were injected into diabetic rats (made diabetic with streptozotocin) and their blood glucose measured over time and compared to glucose levels in a control diabetic rat recieiving conventional soluble form of injectible insulin (Humulin) at a comparable dose. The control rat recieved 1.5 Units of humulin while the rats that were injected with the gel form of insulin recieved doses of 1.5 Units and 7.5 Units respectively. The results of blood glucose over time are reported in the Table below.

| | Blood Glucose mg/dl | | |
| --- | --- | --- | --- |
| TIME, Hours | RAT #1 1.5 Units Humulin | RAT #2 1.5 Units GEL | RAT #3 7.5 Units GEL |
| 0 | 496 | 490 | 448 |
| 0.25 | 462 | 497 | 477 |
| 0.5 | 405 | 463 | 412 |
| 1 | 321 | 417 | 296 |
| 2 | 113 | 140 | 48 |
| 3 | 159 | 94 | 43 |
| 4 | 242 | 74 | 44 |
| 5 | 428 | 237 | 27 |
| 6 | 568 | 185 | 127 |
| 7 | 560 | 219 | 178 |
| 24 | 440 | 461 | 441 |

It can be seen from inspection of the results tabulated herein that the gel form of insulin was able to maintain lower blood sugar for a longer period in the diabetic rats than the control (commercial injectible insulin). This demonstrated clearly the slow release capability of these gels. In addition, it is known that injection of a high dose of insulin, such as 7.5 Units into a rat is lethal due to hypoglycemic toxicity. The high dose injected in this experiment maintained a low blood sugar without lethality again demonstrating that higher doses may be injected in the gel form as a putative depot form of insulin without the risk of hypoglcemic complications.

EXAMPLE 16

Coating of Cell Surfaces with Crosslinked Proteins

Due to the rapidly crosslinkable nature of the modified proteins of the invention, it is possible to form thin coatings of crosslinked proteins around the periphery of living cells. Such coatings would be useful in masking the surface antigens of the coated cell thus preventing an immune response if transplanted in a 'non-self' host. The coating would be permeable to relatively small molecules and nutrients while excluding large molecules such as antibodies of the IgG or IgM class that mediate the immune response.

Hepatocytes were exposed to a solution of eosin in saline (0.0005% wt/vol) for five minutes. The cell suspension was centrifuged at 500 g for five minutes and the cell pellet washed twice with saline and centrifuged. The cell pellet was then resuspended in a physiological solution containing 15% (wt/vol) modified albumin and triethanol amine (0.5% v/v). The suspension was exposed to visible light from a high pressure Hg lamp for 2 minutes. As the eosin diffused away from the cells, a thin coat of crosslinked albumin was formed in the region immediately surrounding the cell where all the essential components for the polymerization were present. Excess saline was then added to the suspension whereby the unreacted protein was dissolved and washed away. Following a wash with saline the cells were returned to culture. Coats of crosslinked protein of thickness from a few microns to tens of microns could be obtained by this method. Surface coatings of gelatin or collagen could be prepared by a similar method.

EXAMPLE 17

Microcarrier Culture and Coating (Immunoprotection)

Cells cultured on microcarriers as described above in the case of hepatocytes may be further coated with a layer of crosslinked protein. The method of Example 16 for cell coating can be utilized for coating of microsphere-attached cells. Such a coating would be beneficial not only in protecting the coated cell from an immune response after transplantation but also in extracoporeal devices such as a liver assist device. In such a device, blood form a patient in liver failure is passed through a device where the plasma is separated from the blood cells and passed through a bed of encapsulated or coated hepatocytes that provide the function of detoxification that is compromised in the patient. The cell coating in this case prevents exposure of circulating antibodies in the patients plasma to the foreign cell-surface antigens that may result in complement activation and subsequent detrimental effects while allowing for exchange and metabolization of circulating toxins.

EXAMPLE 18

Cell Coating with Gelatin—Using Charge Interactions

Most cell surfaces have a net negative charge due to the presence of glycosylated proteins that typically are present on the exterior of the cell membrane. A positively charged polymer therefore will readily bind to the cell surface through ionic interactions with negatively charged groups. For example a protein such as gelatin type A (net positive charge at neutral pH) will bind to the exterior of the cells. Also synthetic polycations such as polylysine have the same effect. Following the attachment of positively charged polymer or protein at the cell surface (now the cell has a net positive surface charge—this can be determined by electrophoretic mobility or zeta potential measurements) a modified gelatin (with substituted photocrosslinkable groups) with net negative charge can be anchored at this cell surface through charge interactions. The cells are then washed in saline, resuspended in a solution containing the photoinitiators and exposed to visible light when polymerization of the modified gelatin at the exterior of the cell is polymerized to form a thin crosslinked coating. Other modified crosslinkable proteins may be utilized for this method of coating.

EXAMPLE 19

Rapidly Photocrosslinkable Proteins for the Prevention of Post-Operative Adhesions/Glue Postoperative adhesions, or filmy connective or scar tissue bridges formed during the normal healing process following surgery, often result in bowel obstructions and infertility arising from kinking of fallopian tubes following abdominal surgery. The isolation of wounded tissue (as a result of surgery) by use of a physical barrier between this tissue and the surrounding organs has been shown to alleviate these problems. Viscous solutions of hyaluronic acid (HA, a polysaccharide) have been used previously for this purpose, albeit in a soluble form. As expected, even these fairly viscous solutions of HA are likely to dissolve away, resulting in the eventual formation of adhesions. The use of in situ photocrosslinkable solutions of a protein such as albumin resulting, in the formation of a cohesive gel around the injured tissue, is likely to efficiently isolate the injured tissue from surrounding organs and thus prevent the formation of adhesions. The use of crosslinkable albumin, a protein that does not elicit an adhesive response from cells and is degradable in vivo to harmless by-products, is advantageous over the use of synthetic materials in vivo. In addition, combinatins of this crosslinkable albumin with hyaluronic acid and/or crosslinkable hyaluronic acid are also likely to prevent the formation of adhesion.

EXAMPLE 20

Interpentrating Polymer Networks of Modified Albumin and Alginates

Alginates have been utilized in the encapsulation of living cells and tissue due to their inherent ionically crosslinkable nature. This provides extremely mild and gentle conditions for encapsulation. Such conditions are particularly favorable for living systems. Alginate gels crossliked with multivalent cations, such as calcium, are particularly porous and easily allow diffusion of large macromolecules through the crosslinked alginate matrix. It is beneficial in certain cases to limit this porosity. By addition of suitable quantities of modified albumin (as described above) to a solution of alginate, followed by ionic crosslinking of the alginate and covalent crosslinking of the albumin by free radical photoinitiation, it is possible to obtain a crosslinked matrix that comprises two components; the alginate ionically crosslinked to itself and the albumin covalently crossslinked to itself. The two polymeric components however are intimately intertwined in the crosslinked state without being chemically linked to each other. Such a physical state is called an Interpenetrating Polymer Network (IPN).

It must also be noted that for a particular protein used in the mixture, only a particular narrow range of compositions (i.e., alginate to Protein ratios) are effective to achieve the desired dual ionic and covalent crosslinking properties. This is because at low protein concentrations (relative to alginate) there is not enough protein present to produce enough crosslinks to stabilize the gel, while at high protein concentrations (relative to alginate), a steric hindrance develops that prevents the alginate from (ionically) crosslinking to itself. Thus an intermediate range or window of concentrations (or ratios) of the two species should be determined, for each protein, so that the resulting mixture will have this dual crosslinking property. The following table shows this data for an alginate/albumin IPN:

| Alginate/Modified Albumin Ratio* | Physical Property of mixture in 0.4% $CaCl_2$** | Physical Property of mixture upon exposure to light 30 seconds*** |
|---|---|---|
| 1:1 | Coherent gel | No gel |
| 1:2 | Coherent gel | soft gel |
| 1:3 | Coherent gel | coherent gel |
| 1:4 | Soft gel | coherent gel |
| 1:5 | No gel | coherent gel |

*The final concentration of alginate in the mixture (solution containing alginate and modified albumin {80% of lysines modified}) was 1.5%.
**The mixture was dropped into a bath of $CaCl_2$ through a syringe and observed for spontaneous formation of dicrete ionically crosslinked droplets or gelled spheres.
***The appropriate photoinitiators were added to the mixture and it was exposed to a 100 watt Hg lamp. The mixture was examined for the formation of a crosslinked gel mass.

Thus, mixtures containing alginate and modified albumin that showed gelling under both conditions, i.e., exposure to calcium as well as exposure to light, were considered to be of utility for encapsulation of living material. Thus ratios in the range of 1:2 to 1:4 were found to be useful for the modified albumin used in this assay.

A mixture of alginate and modified albumin in the useful range, containing the appropriate photoinitiators, was then injected into a solution of calcium chloride ($CaCl_2$), where discrete droplets (ionically crosslinked) were formed. This suspension of droplets was exposed to visible light from a Hg lamp which caused the ionically crosslinked gel to further be stabilized by covalent crosslinking of the albumin component. This was verified by exposing the dually crosslinked droplets to a solution of sodium citrate (1.0 M, a calcium chelator) following ionic and photocrosslinking. Dissolution or fragmentation of the dually crosslinked gels under these rigorous conditions was considered to reflect a failure of adequate photochemical crosslinking, which would have to be sufficient to stabilize the gel in spite of degelling of alginate caused by sodium citrate. In each case the droplets remained stable in citrate, indicating the presence of a crosslinked network other than that provided by ionically crosslinked alginate. Useful ratios of these mixtures clearly would vary and be dependent on the degree of modification of the albumin as well as the protein utilized in generating the IPNs.

EXAMPLE 21

Encapsulation of Islets of Langerhans in IPN Capsules

Islets of langerhans isolated from dogs, rats, pigs, or humans were obtained by techniques described in the art and maintained in culture. A solution of alginate and modified albumin containing the appropriate photoinitiators was prepared with pH 7.4 and osmolarity 300 mOsm/kg. Prior to encapsulation, the islets were washed in saline and precipitated as a pellet by centrifugation. This pellet was resuspended in the alginate-modified albumin mixture at a concentration of approximately 5000 islets/ml of solution. This suspension was pumped through a coaxial flow jethead with concentric air flow to produce droplets of a desired size. Droplets produced by this technique were typically 200–700 microns in diameter. The droplets were collected in a beaker containing calcium chloride solution where they instantly gelled by ionic crosslinking on contact with the solution. The transparent glass collection vessel was exposed to a light source (Hg lamp, 100 watt).

The ionically crosslinked capsules were simultaneously polymerized or photocrosslinked upon exposure to light. This resulted in dually crosslinked droplets or capsules containing islets. Exposure of these cells to light was limited to about five minutes, although no evidence of deterioration or damage to islet function was observed at longer times. The capsules were thoroughly rinsed in saline and culture media and then put into culture.

Alternately large capsules (order of mm) could be prepared by injecting the solution through a syringe. Also, microcapsules prepared by conventional tecniques could be further encapsulated in a 'macrocapsule' by this technique.

EXAMPLE 22

Encapsulation of Hepatocytes in IPN Capsules

Hepatocytes were isolated from Sprague-Dawley rats by conventional methods of collagenase. A solution of alginate and modified albumin containing the appropriate photoinitiators was prepared with pH 7.4 and osmolarity 300 mOsm/kg. Prior to encapsulation, the hepatocytes were washed in saline and precipitated as a pellet by centrifugation. The cell pellet (0.2 ml) was resuspended in 1 ml of the encapsulation solution. This suspension was pumped through a coaxial flow jethead with concentric air flow to produce droplets of a desired size. Droplets produced by this technique were typically 200–700 microns in diameter. The droplets were collected in a beaker containing calcium chloride solution where they instantly gelled by ionic crosslinking on contact with the solution. The transparent glass collection vessel was exposed to a light source (Hg lamp, 100 watt).

The ionically crosslinked capsules were simultaneously polymerized or photocrosslinked upon exposure to light. This resulted in dually crosslinked droplets or capsules containing islets. Exposure of these cells to light was limited to about five minutes, although no evidence of deterioration or damage to islet function was observed at longer times. The capsules were thoroughly rinsed in saline and culture media and then put into culture.

Alternately large capsules (order of mm) could be prepared by injecting the solution through a syringe. Also, microcapsules prepared by conventional techniques could be further encapsulated in a 'macrocapsule' by this technique.

While the invention has been described in detail with reference to certain preferred embodiments thereof, it will be understood that modifications and variations are within the spirit and scope of that which is described and claimed.

---

That which is claimed is:

1. A chemically modified polypeptide having the formula:

$$P—(A—C(O)—Y)n$$

wherein:
P is a non-denatured protein selected from the group consisting of albumin, casein, fibronectin, vitronectin, laminin, fibrinogen, hirudin, proinsulin, muramyl dipeptide, α-1 antitrypsin, α-2-macroglobulin, lactalbumin, and ovalbumin, A is —O—, —S—, or —NR—, wherein R is hydrogen or lower alkyl, wherein A, in combination with a carbonyl moiety, directly links Y to P, Y is:
—C(R)=CR'$_2$, or
—C≡CR' wherein:
R is hydrogen, lower alkyl or substituted lower alkyl, and
R' is hydrogen or lower alkyl, and n is at least 1, and wherein said chemically modified polypeptide is capable of homopolymerizing under conditions that are nontoxic to living cells.

2. A chemically modified polypeptide according to claim 1 wherein P is albumin or casein.

3. A chemically modified polypeptide according to claim 1 wherein each R' is hydrogen.

4. A chemically modified polypeptide according to claim 3 wherein Y is —CH=CH$_2$.

5. A chemically modified polypeptide according to claim 1 wherein n falls in the range of 1 up to about 500.

6. A pre-polymerization mixture comprising:
a) living cell(s) and
b) a chemically modified polypeptide having the formula:

$$P—(A—C(O)—Y)n$$

wherein:
P is a non-denatured protein selected from the group consisting of albumin, casein, pepsin, trypsin, chymotrypsin, fibronectin, vitronectin, laminin, lipase, hemoglobin, lysozyme, immunoglobulins, fibrinogen, transferrin, interleukin-1, interleukin-2, tissue necrosis factor, colony-stimulating factor, epidermal growth factor, transforming growth factors, fibroblast growth factor, insulin-like growth factors, hirudin, tissue plasminogen activator, urokinase, streptokinase, erythropoietin, Factor VIII, Factor IX, insulin, somatostatin, proinsulin, macrophage-inhibiting factor, macrophage-activating factor, muramyl dipeptide, interferons, glucocerebrosidase, calcitonin, oxytocin, growth hormone, α-1 antitrypsin, superoxide dismutase, α-2-macroglobulin, lactalbumin, ovalalbumin and amylase, A is —O—, —S—, or —NR—, wherein R is hydrogen or lower alkyl, wherein A, in combination with a carbonyl moiety, directly links Y to P, Y is:
—C(R)=CR'$_2$, or
—C≡CR' wherein:
R is hydrogen, lower alkyl or substituted lower alkyl, and
R' is hydrogen or lower alkyl, n is at least 1, and wherein said chemically modified polypeptide is capable of homopolymerizing in 100 seconds or less under conditions that are nontoxic to living cells.

7. An article comprising a crosslinked, chemically modified polypeptide having biologically active material entrapped therein, said chemically modified polypeptide having the formula:

$$P—(A—C(O)—Y)n$$

wherein:
P is a non-denatured protein selected from the group consisting of albumin, casein, pepsin, trypsin, chymotrypsin, fibronectin, vitronectin, laminin, lipase, hemoglobin, lysozyme, immunoglobulins, fibrinogen, transferrin, interleukin-1, interleukin-2, tissue necrosis factor, colony-stimulating factor, epidermal growth factor, transforming growth factors, fibroblast growth factor, insulin-like growth factors, hirudin, tissue plasminogen activator, urokinase, streptokinase, erythropoietin, Factor VIII, Factor IX, insulin, somatostatin, proinsulin, macrophage-inhibiting factor, macrophage-activating factor, muramyl dipeptide, interferons, glucocerebrosidase, calcitonin, oxytocin, growth hormone, α-1 antitrypsin, superoxide dismutase, α-2-macroglobulin, lactalbumin, ovalbumin and amylase, A is —O—, —S—, or —NR—, wherein R is hydrogen or lower alkyl, wherein A, in combination with a carbonyl moiety, directly links Y to P, Y is:
—C(R)=CR'$_2$, or
—C≡CR' wherein:
R is hydrogen, lower alkyl or substituted lower alkyl, and
R' is hydrogen or lower alkyl, n is at least 1, and wherein said article is formed in the substantial absence of free monomer.

8. An article according to claim 7 wherein P is albumin, casein, fibronectin, vitronectin, laminin, fibrinogen, hirudin, proinsulin, muramyl dipeptide, α-1 antitrypsin, α-2-macroglobulin, lactalbumin, or ovalbumin.

9. An article according to claim 7 wherein P is albumin or casein.

10. A chemically modified polypeptide according to claim 1, wherein n is not greater than 6.

11. A chemically modified polypeptide according to claim 1, wherein n is greater than 10 but not greater than 500.

12. An article according to claim 7 wherein said biologically active material is an analgesic agent, an anti-asthmatic agent, an antibiotic, an anti-depressant, an anti-diabetic agent, an anti-fungal agent, an anti-hypertensive agent, an anti-inflammatory agent, an anti-neoplastic agent, an immunosuppressive agent, or a physiologically active gas.

13. A chemically modified polypeptide having the formula:

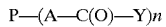

P—(A—C(O)—Y)n wherein:
P is selected from the group consisting of albumin, casein, fibronectin, vitronectin, laminin, fibrinogen, hirudin, proinsulin, muramyl dipeptide, α-1 antitrypsin, α-2-macroglobulin, lactalbumin, and ovalbumin, A is —NR—, wherein R is hydrogen or lower alkyl, wherein A, in combination with a carbonyl moiety, directly links Y to P, Y is:
—C(R)=CR'$_2$, or
—C≡CR'
wherein:
R is hydrogen, lower alkyl or substituted lower alkyl, and
R' is hydrogen or tower alkyl, and
n is at least 1, and
wherein said chemically modified polypeptide is capable of homopolymerizing under conditions that are nontoxic to living cells.

14. A chemically modified polypeptide according to claim 13 wherein R is hydrogen.

15. A chemically modified polypeptide having the formula:

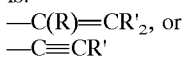

P—(A—C(O)—Y)n wherein;
P is selected from the group consisting of albumin, casein, fibronectin, vitronectin, laminin, fibrinogen, hirudin, proinsulin, muramyl dipeptide, α-1 antitrypsin, α-2-macroglobulin, lactalbumin, and ovalbumin, A is —O—, —S—, or —NR—, wherein R is hydrogen or lower alkyl, wherein A, in combination with a carbonyl moiety, directly links Y to P, Y is—C≡CH,
n is at least 1,and
wherein said chemically modified polypeptide is capable of homopolymerizing under conditions that are nontoxic to living cells.

16. A chemically modified polypeptide having the formula:

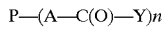

P—(A—C(O)—Y)n wherein:
P is selected from the group consisting of albumin, casein, fibronectin, vitronectin, laminin, fibrinogen, hirudin, proinsulin, muramyl dipeptide, α-1 antitrypsin; α-2-macroglobulin, lactalbumin, and ovalbumin, A is —S—, wherein A, in combination with a carbonyl moiety, directly links Y to P, Y is:
—C(R)=CR'$_2$, or
—C≡CR'
wherein:
R is hydrogen, lower alkyl or substituted lower alkyl, and
R' is hydrogen or lower alkyl, and
n is at least 1, and
wherein said chemically modified polypeptide is capable of homopolymerizing under conditions that are nontoxic to living cells.

17. An article comprising a crosslinked, chemically modified polypeptide having biologically active material entrapped therein, said chemically modified polypeptide having the formula:

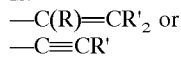

P—(A—C(O)—Y)n wherein:
P is albumin, casein, pepsin, trypsin, chymotrypsin, fibronectin, vitronectin, laminin, lipase, hemoglobin, lysozyme, immunoglobulins, fibrinogen, transferrin, interleukin-1, interleukin-2, tissue necrosis factor, colony-stimulating factor, epidermal growth factor, transforming growth factors, fibroblast growth factor, insulin-like growth factors, hirudin, tissue plasminogen activator, urokinase, streptokinase, erythropoietin, Factor VIII, Factor IX, insulin, somatostatin, proinsulin, macrophage-inhibiting factor, macrophage-activating factor, muramyl dipeptide, interferons, glucocerebrosidase, calcitonin, oxytocin, growth hormone, α-1 antitrypsin, superoxide dismutase, α-2-macroglobulin, lactalbumin, ovalbumin or amylase, A is —O—, —S—, or —NR—, wherein R is hydrogen or lower alkyl, wherein A, in combination with a carbonyl moiety, directly links Y to P, Y is —C≡CH
n is at least 1, and
wherein said article is formed in the substantial absence of free monomer.

18. An article comprising a crosslinked, chemically modified polypeptide having a growth factor entrapped therein, said chemically modified polypeptide having the formula:

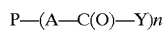

P—(A—C(O)—Y)n wherein:
P is albumin, casein, pepsin, trypsin, chymotrypsin, fibronectin, vitronectin, laminin, lipase, hemoglobin, lysozyme, immunoglobulins, fibrinogen, transferrin, interleukin-1, interleukin-2, tissue necrosis factor, colony-stimulating factor, epidermal growth factor, transforming growth factors, fibroblast growth factor, insulin-like growth factors, hirudin, tissue plasminogen activator, urokinase, streptokinase, erythropoietin, Factor VIII, Factor IX, insulin, somatostatin, proinsulin, macrophage-inhibiting factor, macrophage-activating factor, muramyl dipeptide, interferons, glucocerebrosidase, calcitonin, oxytocin, growth hormone, α-1 antitrypsin, superoxide dismutase, α-2-macroglobulin, lactalbumin, ovalbumin or amylase, A is —O—, —S—, or —NR—, wherein R is hydrogen or lower alkyl, wherein A, in combination with a carbonyl moiety, directly links Y to P, Y is:
- —C(R)=CR'$_2$, or
- —C≡CR' wherein:

R is hydrogen, lower alkyl or substituted lower alkyl, and

R' is hydrogen or lower alkyl, n is at least 1, and wherein said article is formed in the substantial absence of free monomer.

* * * * *

UNITED STATES PATENT AND TRADEMARK OFFICE
CERTIFICATE OF CORRECTION

PATENT NO.    : 6,565,842 B1  Page 1 of 1
DATED         : May 20, 2003
INVENTOR(S)   : Soebianto A. Sojomihardjo et al.

It is certified that error appears in the above-identified patent and that said Letters Patent is hereby corrected as shown below:

<u>Column 35,</u>
Line 38, change "tower" to -- lower --

Signed and Sealed this

Nineteenth Day of August, 2003

JAMES E. ROGAN
*Director of the United States Patent and Trademark Office*

SEQUENCE LISTING

<160> NUMBER OF SEQ ID NOS: 19

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Tyr Ile Gly Ser Arg
 1               5

<210> SEQ ID NO 2

```
<211> LENGTH: 4
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Arg Glu Asp Val
  1

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Pro Asp Ser Gly Arg
  1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Ile Lys Val Ala Val
  1               5

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Arg Asp Gly Phe
  1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gly Arg Gly Asp
  1

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7
```

Arg Gly Asp Tyr
1

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gly Arg Gly Asp Tyr
1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gly Tyr Ile Gly Ser Arg
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gly Tyr Ile Gly Ser Arg Tyr
1               5

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Arg Gly Asp Ser
1

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gly Arg Glu Asp Val
1               5

<210> SEQ ID NO 13
<211> LENGTH: 6
<212> TYPE: PRT
<213> ORGANISM: Artificial Sequence
<220> FEATURE:

```
<223> OTHER INFORMATION: Description of Artificial Sequence: Synthetic
      polypeptide

<400> SEQUENCE: 13

Gly Arg Glu Asp Val Tyr
  1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gly Arg Gly Asp Phe
  1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gly Pro Asp Ser Gly Arg
  1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gly Pro Asp Ser Gly Arg Tyr
  1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gly Ile Lys Val Ala Val
  1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Ile Lys Val Ala Val Tyr
  1               5
```

```
<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gly Ile Lys Val Ala Val Tyr
1               5
```